United States Patent [19]

Long

[11] Patent Number: 5,548,651
[45] Date of Patent: Aug. 20, 1996

[54] STEREOPHONIC STETHOSCOPE

[76] Inventor: Howard F. Long, 363 St Mary St., Pleasanton, Calif. 94566

[21] Appl. No.: 218,522

[22] Filed: Mar. 28, 1994

[51] Int. Cl.⁶ .............................. A61B 7/04; A61B 7/02; A61B 5/02
[52] U.S. Cl. ............................ 381/67; 181/131; 128/715; D24/134
[58] Field of Search .............................. 381/67; 181/126, 181/131; 128/715; D24/134

[56] References Cited

U.S. PATENT DOCUMENTS

| | | | |
|---|---|---|---|
| 3,160,708 | 12/1964 | Andries | 179/1 ST |
| 3,790,712 | 2/1974 | Andries | 179/1 ST |
| 4,071,694 | 1/1978 | Pfeiffer | 179/1 ST |
| 4,072,822 | 2/1978 | Yamada | 179/1.5 T |
| 4,254,302 | 3/1981 | Walshe | 179/1 ST |
| 4,438,772 | 2/1984 | Slavin | 128/715 |
| 4,534,058 | 8/1985 | Hower | 381/67 |
| 4,618,986 | 10/1986 | Hower | 381/67 |
| 4,706,777 | 11/1987 | Baumberg | 181/131 |
| 4,770,189 | 9/1988 | Shyu | 381/67 |
| 4,777,961 | 10/1988 | Saltzman | 128/715 |
| 4,878,501 | 11/1989 | Shue | 128/715 |
| 4,940,023 | 7/1990 | Shue | 128/715 |
| 4,997,055 | 3/1991 | Grady | 181/131 |
| 5,007,091 | 4/1991 | Alsaarela et al. | 381/26 |
| 5,076,284 | 12/1991 | Joyce et al. | 128/715 |
| 5,218,969 | 6/1993 | Bredesen et al. | 381/67 |
| 5,367,575 | 11/1994 | Dieken et al. | 381/67 |

FOREIGN PATENT DOCUMENTS 2147475  5/1985  United Kingdom .................. 181/126

Primary Examiner—Forester W. Isen
Assistant Examiner—Xu Mei

[57] ABSTRACT

An electronically amplified, recording, stereophonic stethoscope, EARSS, utilizes binaural phase effect from two probes held in one chestpiece with amplifier. Skin contacts in probes are small, to localize, pliable, to fit body curves, shaped for acoustic amplification, spread for wide pickup. Connecting tubes are flexible, with dimensions and properties that protect, isolate, reinforce and adapt skin contacts to microphones. Adapters for multiple stereophones, listeners, recorders, videocameras and imaging of induced sound, facilitate teaching, consultation and sharing with patients. More sensitive and specific detection and recognition of diseases and functions stimulate more careful auscultation by physicians, new uses and tests, and increased lay use of a classic professional symbol.

3 Claims, 3 Drawing Sheets

STEREOPHONIC STETHOSCOPE

BACKGROUND FIELDS OF THE INVENTION

The fields of this invention are stethoscopes, electronic stethoscopes and scientific devices, 128/715, 381/67 and 179/1.

BACKGROUND OF THE INVENTION

Stereophonic hearing, binaural phase effect with two ears for direction and distance, has guided owls, elephants, blind people and my 160,000 chest examinations. Over 1,000 examinations have now been, not only stereophonic, but also electronically amplified.

The traditional stethoscope, although called binaural and having 2 earpieces, receives sound from a single chest piece. For 40 years, I have used two chestpieces, one connected to each ear, first through flexible tubing, then through the customary metal tubing joined by a spring. Faster, better examination with that stereophonic stethoscope caused me to use it with almost every patient visit in my family practice.

Decreased hearing stimulated development of an amplified stereophonic stethoscope, necessity the mother of further invention. I devised and tested thousands of new parts and combinations: skin contacts of various shapes, sizes and materials with tubes of various sizes, lengths and materials connected to microphones and to shielded cables of various lengths and to various stereo amplifiers, stereo earphones and instruments. A preferred embodiment described here is more convenient to carry and use than a traditional stethoscope and expands auscultation with a whole new dimension.

Vivid sound image from amplification with spatial orientation makes auscultation more productive. Stroke has been prevented, by detection of severe carotid obstruction, not found otherwise. New uses are stimulated; epigastric bruit from ovary hyperemia, normal when egg-making, may indicate early ovary cancer at other times, a much needed screening test (Nat Cancer Inst letter, encl).

Lay interest and cooperation is aroused by hearing one's body with one's doctor. Patients ask where to buy one to monitor a child's asthma or bruit of inflammation. Unexpected vividness, of directional, three dimensional sound with electronically amplified, recording, stereophonic stethoscope, EARSS, stimulates the art and science of auscultation.

DESCRIPTION OF THE INVENTION

A stereophonic stethoscope utilizes binaural phase effect from two probes. An electronically amplified, recording, stereophonic stethoscope, EARSS, has two probes held in one chestpiece with amplifier. Skin contacts in probes are small to localize, pliable to fit body curves, shaped for acoustic amplification, spread for wide pickup. Connecting tubes are flexible, with dimensions and properties that protect, isolate, reinforce and adapt skin contacts to microphones. Adapters for multiple stereophones, listeners, recorders, videocameras and imaging of induced sound, facilitate teaching, consultation and sharing with patients. More sensitive and specific detection and recognition of diseases and functions stimulate more careful auscultation by physicians, new uses and tests, and increased lay use of a classic professional symbol.

DESCRIPTION OF PRIOR ART

The common binaural stethoscope is not directional, not stereophonic. The one sensor does not transmit direction. Amplification is often inadequate for faint sounds or heavy persons. The Andties electronic stethoscope, U.S. Pat. Nos. 190 3,160,708 and #3,790,712, and some others listed, do improve amplitude, multiple use and recordability. However, no stethoscope found in prior art gives direction of sounds, localization, depth or third dimension except Baumberg, U.S. Pat. No. #4,706,777, which is not electronically amplified. Grady U.S. Pat. No. #4,997,055, and Joyce, U.S. Pat. No. #5,076,284 have multiple sensors, but mix signals in a single tube or wire at some point, so lack stereophonic use. Grady is not amplified electronically. Joyce uses compressed air, not electronics.

Chestpieces claimed to be superior by Artdries, Pfeiffer, Yamaria, Walshe, Hower, Saltzman and Shue are all so large as to be unwieldy, if two were used stereophonically. Prior an chestpieces do not fit comfortably onto curves - anatomical undulations like the carotid crease or between ribs. Advantages claimed by prior an above, like change to acoustic and choice of type or size of chestpiece, are superfluous with an amplified, stereophonic stethoscope with multiple use, small probes. The differential stethoscope of Slavin, U.S. Pat. No. #4,438,772, subtracts the signal of one skin contact from the signal of the other to reduce noise. The differential stethoscope does not integrate; each ear receives the same signal through a common tube or wire, losing localization. Differential stethoscope, like all other prior art, is not an electronically amplified, recording, stereophonic stethoscope, EARSS.

DESCRIPTION OF DRAWINGS

Figure 1:
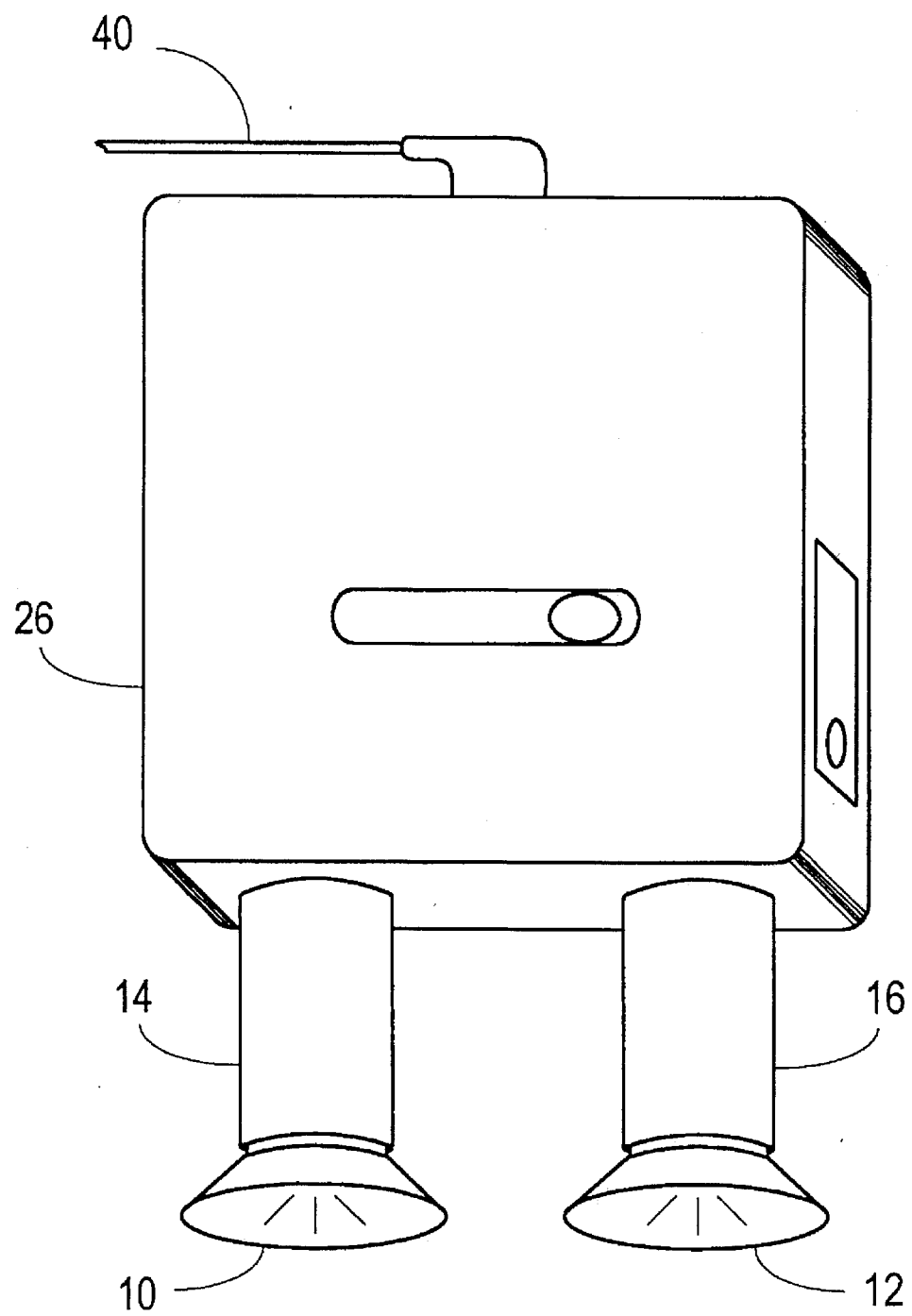
FIG. 1. A Preferred Embodiment.
Figure 2:
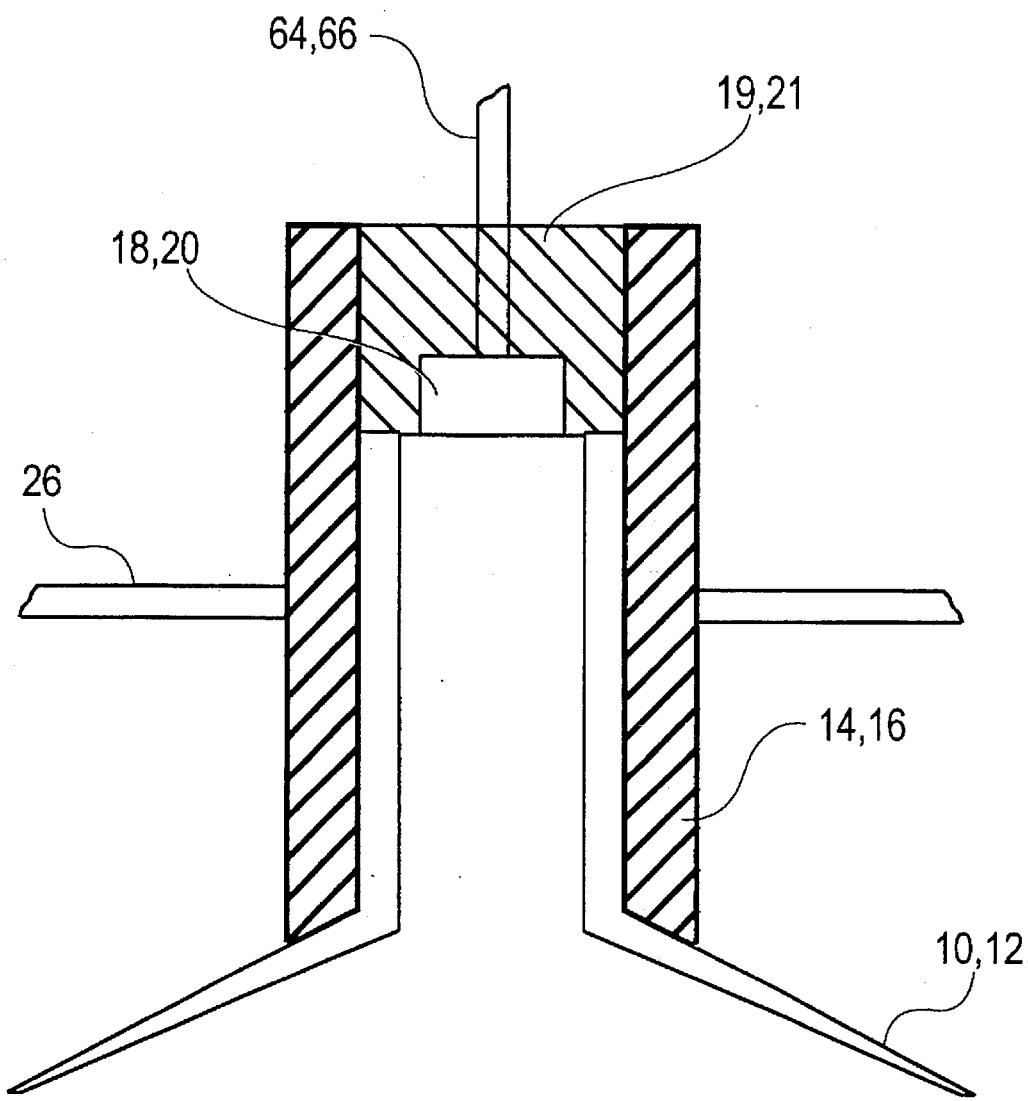
FIG. 2. A Preferred Embodiment Probe - cross-section.
Figure 3:
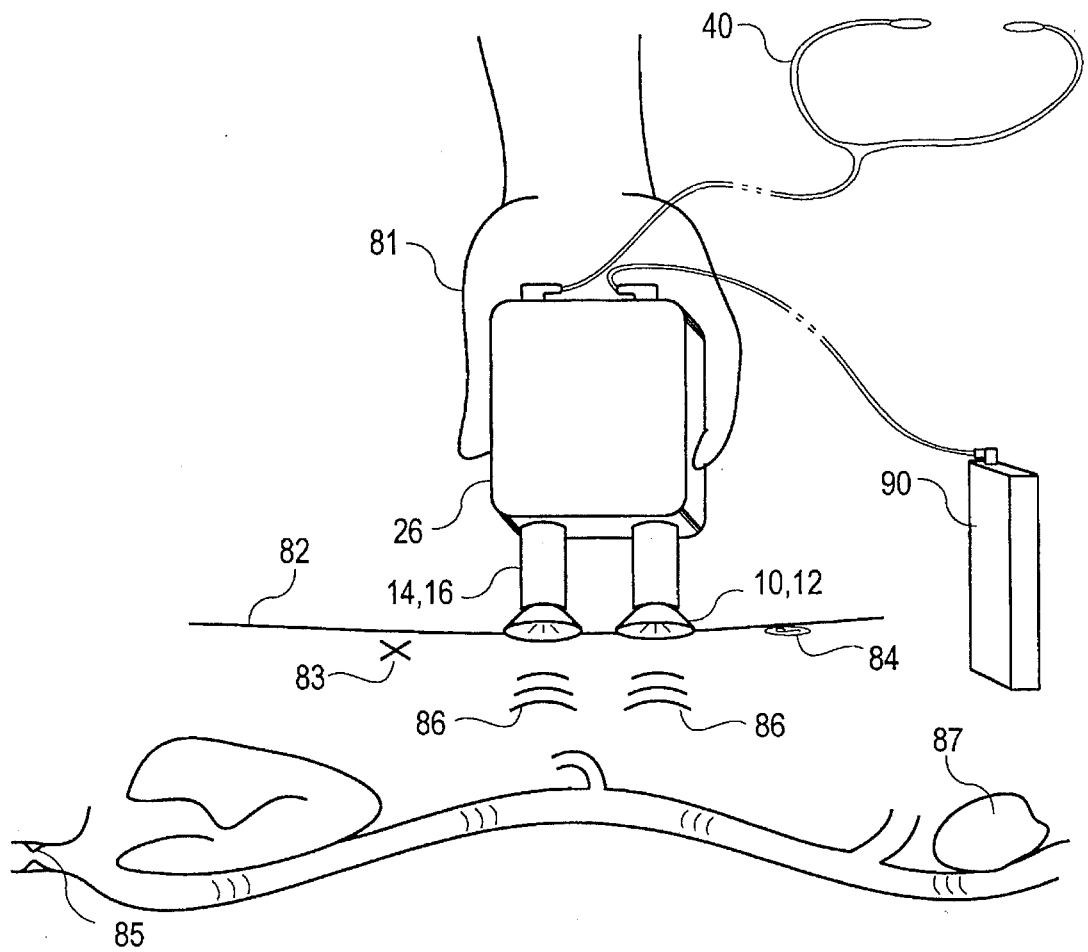
FIG. 3. A Preferred Embodiment - Recording On Abdomen

FIGS. 1, 2, 3. Skin contacts, left (10) and right (12), approximate shape of human ear canals and insert into pliable, support tubes left (14) and right (16), inserted into chestpiece (26), Support tubes (14,16) hold microphones left (18) and right (20), in foam jackets, left (19) and right (21), FIG. 2. Microphone wires left (64) and right (66) go through jackets, connecting to other components and controls of a mini stereoamplifier (26) and stereophone cable (40), FIGS. 1, 2, 3.

In FIG. 1–3, two probes or support tubes (14, 16) and amplifier are within the chestpiece (26), conveniently held in one hand, FIGS. 1, 3. Some stereophones (40) fit into a shirt pocket holding also amplifier with probes, FIGS. 1, 3. Binaural phase effect, sensed by probes, FIG. 2, and enhanced through stereo amplifier within the chestpiece (26) and stereophones, (40), surprises a listener with vivid, three dimensional sound, preserved on various recorders (90), FIG. 3. Note the entirely separate sensors (10,12) and connecting tubes (14,16) for left ear from those for right ear.

CONSTRUCTION OF A PREFERRED EMBODIMENT

1. Disassemble a Radio Shack 33-1093A Stereo Amplified Listener or equivalent (26), FIG. 1.

2. Work segments of tough, pliable connecting tubing (14,16) over microphones (18, 20) and jackets (19, 21) FIGS. 1, 2.

3. Drill holes in amplifier casing, in the section having volume slot, and opposite positions of microphones (18,20), FIGS. 1, 2.

4. Push tubes (14,16) through drill holes.

5. Insert skin contacts (10,12) into connecting tubes (14,16).

6. Insert choice of stereophonic earphones, (40) or insert splitter for multiple earphones (40) or recorders (90)

SUMMARY

Stereophonic stethoscope has new features and new combinations of old features, with new and unexpected results. Stereophonic stethoscope succeeds where others failed or failed to recognize need. Vivid, moving sounds surround a listener as if inside the subject. Synergy results are greater than sum of results of references. A stethoscope is the very symbol of a physician; even small advances have been recognized, with 160 patents—a crowded art. Integration of stereophonic music receivers with probes and surface sensors, if suggested, has not previously been developed. Findings from extended, enhanced auscultation give new value to physical examination.

Three dimensional sound images may be observed, including sound shadows of differential reflection from, and transmission through, tissues and objects when sounds are induced by phonation, percussion or other vibration. Recordings of audio, video and graph images are made by stereophonic tape recorder, stereophonic sound for video-tape camera and phonocardiographs for differential analysis or 3-D imaging, synergizing powerful diagnostic, teaching and consulting tools.

What is claimed is:

1. An electronically amplified, recording stereophonic stethoscope (EARSS) adapted to receive auscultatory sound from a patient, comprising:

a chestpiece sized to permit being held in a user's hand;

two separate acoustic support tubes, each having a skin contact on a respective distal end thereof; each proximal end thereof being fixed to said chestpiece and said each proximal end having a microphone mounted thereat for receiving sound from its respective tube;

said two acoustic support tubes are sufficiently rigid to permit both of said skin contacts to be firmly applied to a patient's body for monitoring auscultatory sound while the user holds only said chestpiece;

a stereo amplifier within said chestpiece for amplifying respective outputs of each said microphone to produce left and right electronically amplified output sounds;

at least one pair of stereo headphones receiving said left and right electronically amplified sounds.

2. The electronically amplified, recording stereophonic stethoscope (EARSS) according to claim 1, said chestpiece further comprises signal transmitting means for transmitting the received auscultatory sound to a recording means.

3. The electronically amplified, recording stereophonic stethoscope (EARSS) according to claim 1, wherein said skin contacts are disposable.

* * * * *